United States Patent [19]

Kampfer et al.

[11] Patent Number: 4,883,880

[45] Date of Patent: Nov. 28, 1989

[54] PROCESS FOR THE PREPARATION OF SULFOALKYL QUATERNARY SALTS AND FOR THE PRODUCTION OF ALKANE SULTONES

[75] Inventors: Helmut Kampfer, Cologne; Wolfgang Himmelmann, Leverkusen, both of Fed. Rep. of Germany

[73] Assignee: AGFA-Gevaert Aktiengessellschaft, Leverkusen, Fed. Rep. of Germany

[21] Appl. No.: 520,911

[22] Filed: Aug. 8, 1983

Related U.S. Application Data

[63] Continuation-in-part of Ser. No. 373,986, May 3, 1982, abandoned, which is a continuation-in-part of Ser. No. 440,201, Nov. 18, 1982, abandoned.

[51] Int. Cl.$^4$ .................. C07D 213/18; C07D 327/04; C07D 327/06; C07D 143/42
[52] U.S. Cl. ...................... 546/347; 549/14; 549/40; 562/104; 562/107
[58] Field of Search ............... 546/347; 549/40, 14; 260/509, 512 R

[56] References Cited

U.S. PATENT DOCUMENTS

| | | | |
|---|---|---|---|
| 2,503,776 | 4/1950 | Sprague | 542/452 |
| 3,592,648 | 7/1971 | Keller et al. | 430/140 |
| 3,861,920 | 1/1975 | Borror et al. | 430/560 |
| 4,225,705 | 9/1980 | Bader et al. | 542/452 |

OTHER PUBLICATIONS

P. A. S. Smith, The Chemistry of Open–Chain Organic Nitrogen Compounds, vol. I, pp. 211–214, Benjamin Pub. 1965.
Tokuda I, Chem. Abstracts, vol. 91, (12) abst. No. 92486t, Sep. 17, 1979.
Tokuda II, Chem. Abstracts, vol. 92(3) abst. No. 23,570z, Jan. 21, 1980.
Kitzing et al., Chem. Abstracts, vol. 90, (16), abst. No. 123,078x, Apr. 16, 1979.
Chem. Abstracts, vol. 88(10), abst. No. 63,259d, Mar. 6, 1978.

*Primary Examiner*—Alan L. Rotman
*Attorney, Agent, or Firm*—Connolly and Hutz

[57] ABSTRACT

Propane or butane sultones are prepared by the thermal decomposition of the corresponding aryl sulfoalkyl ethers wherein the alkyl part has three or four carbons between the sulfo group and the ether oxygen. When a tertiary amine is present, the final product is the corresponding sulfoalkyl quaternary salt of the tertiary amine.

13 Claims, No Drawings

PROCESS FOR THE PREPARATION OF SULFOALKYL QUATERNARY SALTS AND FOR THE PRODUCTION OF ALKANE SULTONES

CROSS-REFERENCE

This application is a continuation-in-part of U.S. application Ser. No. 373,986 filed May 3, 1982 by Helmut Kampfer and Wolfgang Himmelmann for Process for the Preparation of Sulfoalkyl Quaternary Salts (still pending) and also a continuation-in-part of U.S. application Ser. No. 440,201 filed Nov. 8, 1982 by the Helmut Kampfer and Wolfgang Himmelmann for Process for the Production of Alkane Sultones (still pending).

This invention relates to a process for the preparation of sulfoalkyl quaternary salts of tertiary amines, in particular of heterocyclic bases containing nitrogen.

Further this inventon relates to a process for the production of alkane sultones, in particular 1,3-propane sultones and 1,4-butane sultones.

Sulfoalkyl Quaternary Salts which contain positively and negatively charged groups connected by covalent bonds are known as betaines. They play an important role in numerous technical processes. They are either used as such, e.g. in electro-plating, or subjected to further reactions as intermediate products. When sulfoalkyl betaines are to be used as intermediate products, it is frequently technically advantageous not first to isolate them but to let the subsequent reaction follow immediately on the process for their preparation. Sulfoalkyl betaines are important intermediate products, for example for the synthesis of polymethine dyes used as spectral sensitizers for light sensitive materials, in particular for photographic silver halide emulsions. The present invention thus also relates to the conversion of the heterocyclic bases to polymethine dyes by way of the sulfoalkyl quaternary salts.

Process for the preparation of sulfoalkyl quaternary salts of tertiary amines have long been known. The tertiary bases are reacted with a sulfoalkylating agent, usually at an elevated temperature. Sulfoalkylating agents include inter alia halogen alkane sulfonic acids, e.g. 2-bromo-ethane sulfonic acids described in U.S. Pat. No. 2,503,776, sodium-iodo-ethane sulfonate described in Belgian Pat. No. 669,308, sodium-iodo-butane sulfate described in U.S. Pat. No. 2,912,329 and 3-chloro-2-hydroxy propane sulfonic acid described in German Auslegeschrift No. 1,177,482. One disadvantage of these sulfoalkylating agents is the excess of tertiary base required to combine with the hydrogen halide formed when free sulfonic acids are used. Sultones are also known as sulfoalkylating agents; thus the use of propane-, butane- and isopentane sultone has been described in German Pat. No. 929,080, of propene sultone in German Auslegesschrift No. 1,447,579 and of 2-chloro-propane sultone in British Pat. No. 1,090,626. One disadvantage of sultones is that some are physiologically harmful so that their use may entail an environmental risk as well as a safety risk for persons handling them.

Sulfoalkylating agents which obviate the use of carcinogenic sultones have recently been described. German Offenlegungsschrift No. 28 25 246 and Research Disclosure 16374 (November 1977) mention hydroxyalkane sulfonic acids and their salts while GDR Pat. No. 139,577 mentions aqueous solutions of hydroxyalkane sulfonic acids and their O-alkyl- and O-acyl-derivatives as quaternizing agents. One disadvantage of these compounds is the considerable quantities of water formed in the reaction, which inhibit quaternization and may result in low yields unless they are removed by azeotropic distillation with suitable solvents.

O-Sulfoalkyl imido esters have been described in Research Disclosure 18040 (April 1979) and related O-sulfoalkyl isouronium betaines in German Offenlegungsschrift No. 29 09 200. These new quaternizing agents also have some disadvantages. Their preparation is relatively expensive since it requires the use of carbodiimides, acid nitriles or dialkyl ureas, their thermal stability is limited and in case of high melting points solvents must be used as reaction medium.

For these reasons it was an object of the present invention to provide a process for the preparation of sulfoalkyl quaternary salts which would not have the disadvantage mentioned above.

A process for the preparation of sulfoalkyl quaternary salts of tertiary amines has now been found, which is characterized by the reaction of tertiary amine with a sulfoalkyl-aryl ether corresponding to the general formula I:

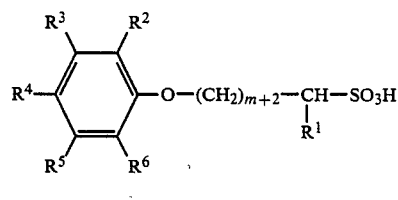

wherein
$R^1$ denotes hydrogen or methyl;
$R^2$, $R^3$, $R^4$, $R^5$ and $R^6$ may be idential or different and denote hydrogen, a lower alkyl group, preferably with one or two C-atoms, halogen, e.g. F, Cl, Br or I, an alkoxy group, preferably $OCH_3$, or a cyano or nitro group (but not more than two nitro groups are present in the phenyl ring); or $R^2$ and $R^3$ together or $R^3$ and $R^4$ together denote the ring members required to complete a condensed, saturated or unsaturated 5-membered or 6-membered ring optionally also containing oxygen or sulfur atom; and
m=0 or 1.

The reaction is carried out at elevated temperature, e.g. at a temperature of from 80° to 250° C., preferably at 140° to 180° C.

The reaction generally proceeds smoothly within the last mentioned temperature range but temperatures outside this range may be employed if necessary, for example on account of the nature of the solvent used.

the tertiary amines used may in principle be any derivatives of ammonia ($NH_3$) in which each of the three hydrogen atoms is substituted, e.g. by a carbon atom of an alkyl or aryl group or by a carbon atom or hetero atom of a heterocyclic ring, and this heterocyclic ring may in particular include the nitrogen atom of the tertiary amine. Particularly preferred heterocyclic bases correspond to the general formula II:

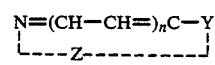

wherein Z denotes the members required for completing a heterocyclic group having at least one 5-membered or 6-membered heterocyclic ring; this hetero ring may have condensed to it benzene, naphthalene or heterocyclic rings which may in turn be substituted. Any of the heterocyclic compounds known from the class of cyanine dyes may be considered, e.g. pyrroline (e.g. 4,4-dimethyl-pyrroline), oxazoline (e.g. 4,4-dimethyl oxazoline), thiazoline (e.g. 5-methyl thiazoline), selenazoline, indoline (e.g. 3,3-dimethyl indoline, 3,3-dimethyl-5-methoxy indoline, and 3,3-dimethyl-5-diethylamino indoline), benzimidazole (e.g. 1-ethyl-5-trifluoromethyl-benzimidazole, 1-methyl-5-chlorobenzimidazole, 1-ethyl-5,6-dichloro-benzimidazole, 1-ethyl-5-cyanobenzimidazole, 1-methyl-5-carbethoxybenzimidazole, 1-ethyl-5-acetyl-benzimidazole, 1-methylbenzimidazole-5-sulfonic acid pyrrolidide, 1-ethylbenzimidazole-5-sulfonic acid dimethylamide, 1-ethyl-5-phenylthio-benzimidazole, 1-methyl-5-methylthio-benzimidazole and 1-methyl-5-chloro-6-methylthio-benzimidazole), oxazole (e.g. 4-methyl oxazole, 4,5-diphenyl oxazole, 4-methyl-5-carbethoxy oxazole, benzoxazole, 5-chlorobenzoxazole, 5-phenyl benzoxazole, 6-methoxy benzoxazole, 5-methoxy benzoxazole, 5-methyl-6-methoxy benzoxazole, 5-bromobenzoxazole, 5-iodobenzoxazole, naphtho[2,1-d]oxazole, naphtho[1,2-]oxazole, naphtho[2,3-d]oxazole, 4,5,6,7-tetrahydrobenzoxazole, and benzofuro[2,3-f]benzoxazole(, thiazole (e.g. 4-methyl-thiazole, 4-phenylthiazole, 4-methyl-thiazole-5-acrylic acid ethyl ester, benzothiazole, 5-methylbenzothiazole, 6-methyl-benzothiazole, 5-chlorobenzothiazole, 5-methoxybenzothiazole, 6-methoxybenzothiazole, 5,6-dimethyl-benzothiazole, 5,6-dimethoxy-benzothiazole, 5-methyl-6-methoxy-benzothiazole, 5-bromobenzothiazole, 5-phenyl-benzothiazole, 6-methylthio-benzothiazole, 6-dimethylamino-benzothiazole, 5-chloro-6-methoxy benzothiazole, 5,6-methylenedioxy-benzothiazole, 6-β-cyanoethoxy-benzothiazole, 5-carbomethoxybenzothiazole, 5-nitrobenzothiazole, 5-phenylthio-benzothiazole, 5-thienyl-benzothiazol, 6-hydroxy-benzothiazole, 4,5,6,7-tetrahydrobenzothiazole, 4-oxo-4,5,6,7-tetrahydrobenzothiazole, naphtho[2,1-d]thiazole, naphtho[1,2-d]thiazole, 4,5-dihydronaphtho[1,2-d]thiazole, 5-methoxy naphtho[1,2-d]thiazole, and 5,7,8-trimethoxy-naphtho[1,2-d]thiazole), selenazole (e.g. benzoxelenazole, 5-methyl-benzoselenazole, 5,6-dimethyl-benzoselenazole, 5-methoxy benzoselenazole, 5-methyl-6-methoxy-benzoselenazole, 5,6-dimethoxy-benzoselenazole, 5,6-methylenedioxy benzoselenazole, 6-methyl-benzoselenazole, and naphtho[1,2-d]selenazole), 1,3,4-oxadiazole (e.g. 5-methoxyl-1,3,4-oxadiazole and 5-phenyl-1,3,4-oxadiazole), 1,3,4-thiadiazole (e.g. 5-methyl-1,3,4-thiadiazole, 2,5-bis-methylthio-1,3,4-thiadiazole, 5-benzylthio-1,3,4-thiadiazole, 2-mercapto-5-methylthio-1,3,4-thiadiazole, and 5-carbethoxymethylthio-1,3,4-thiadiazole), pyridine (e.g. 2-methyl-pyridine and 4-methyl-pyridine), pyrimidine (e.g. 2-methyl-4-methylthio-pyrimidine), quinoline (e.g. 6-methyl-quinoline, 6-methoxy-quinoline, 8-chloroquinoline, 6-fluoroquinoline, 5,6-benzoquinoline, and 6,7-benzoquinoline);and imidazolo[4,5-b]quinoxaline;

n=0 or 1; and

Y denotes hydrogen, halogen, a saturated or unsaturated aliphatic group, in particular having up to 6 C-atoms and optionally substituted e.g. methyl, ethyl, allyl, cyanoalkyl, halogen alkyl, alkoxy, alkoxy alkyl, alkoxy e.g. carboxy alkoxy, alkylthio, e.g. carboxyalkylthio, sulfoalkylthio, carbalkoxyalkylthio, or mercapto.

Y may for example, also denote a methine chain having 1, 3 or 5 methine groups carrying at its end an N-alkylated heterocyclic base usually attached via the 2-position, such as those known from the chemistry of cyanine dyes. Reference may be had in this connection to F. M. Hamer, "The Cyanine Dyes and Related Compounds", (1964), Interscience Publishers John Wiley & Sons. Compounds of the formula II in which Y has the meaning defined above are referred to as "dequaternized cyanine dyes". When such dequaternized cyanine dyes are reacted by the process according to the invention, the products obtained may be directly used as sensitizing dyes without further reactions.

The reactions are generally carried out without solvents, although a suitable solvent may be used. Any solvents which are inert in the reaction according to the invention and which have a high dissolving power for the reactants are suitable for this purpose, e.g. phenol, m-cresol, m-xylene, chlorobenzene, anisole, glacial acetic acid and acetic anhydride. In some cases, as described in greater detail below, it is of advantage first to heat the sulfoalkylating agent to the elevated temperature, e.g. of from 80° to 250° C. and preferably of from 140° to 180° C., before addition of the tertiary amine, and when the tertiary amine is added, to carry out the sulfoalkylating reaction in the described manner.

The reaction according to the invention are accompanied by the splitting off of a phenol corresponding to the formula:

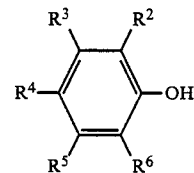

in which the groups $R^2$, $R^3$, $R^4$, $R^5$ and $R^6$ have the meaning already indicated. The nature and size of the substituents $R^2$, $R^3$, $R^4$, $R^5$ and $R^6$ are otherwise significant for the process according to the present invention only to the extent that they should not impair the thermal decomposition of the sulphoalkyl-arylethers and, where applicable, the removal of the phenols which have been split off. It will therefore be necessary to ensure that these substituents are sufficiently small so that the phenols released in the course of thermal decomposition may easily be removed by distillation.

The ethers according to the invention are in most cases reacted with the bases in a molar ratio of 1:1, and 1 mol of phenol is formed per mol of base, although the reaction may also be carried out with different molar ratios, e.g. 2:1. Owing to its high dissolving power for the quaternary salts formed in the reaction, the phenol formed prevents solidification of the reaction mixture and thereby greatly facilitates the technical application of the process. As described in greater detail below, any excess of phenol formed may be removed from the reaction vessel, for example by (1) operating under vacuum, (2) introducing an anhydrous inert gas, e.g. nitrogen, or (3) evaporating off the phenol or freezing it out in a freezing apparatus.

The sulfobetaines of tertiary amines prepared by the process according to the invention include in particular those corresponding to the following formula III:

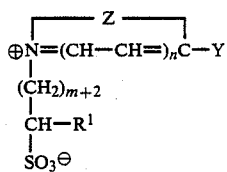

wherein n, m, Y, Z and $R^1$ have the meaning already indicated.

These compounds may be used for various purposes, for example as conductive salts in electroplating. These compounds may also be end products of a cyanine dye synthesis if Y has a suitable meaning, i.e. when it represents a methine chain having 1, 3 or 5 methine groups with an N-alkylated heterocyclic base at the end, as already mentioned above. Such compounds are used directly for the spectral sensitization of light-sensitive silver halide emulsions but when Y has another meaning within the definition given above the compounds prepared by the process according to the invention are also important intermediate products for the synthesis of polymethine dyes. Thus, for example, the sulfoalkyl quaternary salts of heterocyclic bases prepared by the process acording to the invention are advantageously not isolate but immediately reacted, without further purification to produce polymethine dyes in known manner after termination of the quaternizing reaction.

The ethers (I) used according to the invention are already known in principle. They may be prepared from phenols and suitable sultones by heating to 130° to 140° C. (see K. Furukawa et al, Kogyo Kagaku Zasshi 59, 221–224 (1956) or from phenols and sultones in the presence of alkali metal hydroxide in alcoholic solution (see J. H. Helberger et al, Liebigs Ann. Chem. 565, 28 (1949), 586, 147, 150, 157, 163 (1954)). Another method synthesis is the reaction of halogen alkane sulfonic acids with phenols in the presence of alkali. Still another method of synthesis is the reaction of ω-halogenalkyl-aryl ethers with $Na_2SO_3$ (see Schenck and Kaizerman, J. Amer. Chem. Soc. 75, 1636, 1641 (1953)).

EXAMPLE OF PREPARATION 1

(3-sulfopropyl)-phenyl-ether (Ether 1)

60 g of propane sultone in 350 ml of ethanol are added to 60 g of sodium phenolate in 250 ml of ethanol in the course of one hour. The temperature of the reaction mixture rises to 30° C. in the course of this addition and the mixture is then stirred for 1 hour at 60° to 65° C. The reaction mixture is suction-filtered after cooling and washed with ethanol.

Yield: 90 g of the sodium salt of ether 1 (85% of theoretical yield).

The free sulfonic acid is isolated from the aqueous solution of the sodium salt by means of cation exchangers. It is dried under vacuum at 100° C. to yield a crystallizing oil.

Mp. 70° to 72° C.

EXAMPLE OF PREPARATION 2

(3-sulfopropyl)-(3-methylphenyl)-ether (Ether 2)

108 g of m-cresol in 250 ml of methanol and 56 g of potassium hydroxide are stirred until dissolved. Stirring is continued for one more hour after the addition of 122 g of propane sultone in 500 ml of methanol and the reaction mixture is then cooled, separated by suction filtration and the product is washed with methanol.

Yield: 83.5% = 192 g of the potassium salt of Ether 2. When the potassium salt is dissolved in water and used to charge a cation exchanger column, an aqueous solution of the free acid is obtained. When this acid is evaporated to dryness under vacuum at 40° C., a crystallizing oil is obtained from it.

The following ethers were prepared in analogous manner.

(3-sulfopropyl)-(3-methyl-4-chlorphenyl)-ether (Ether 3), Mp. 43°–50° C.;

(3-sulfopropyl)-(4-methylphenyl)-ether (Ether 4), Mp. 74°–45° C.;

(3-sulfopropyl)-(1-naphthyl)-ether (Ether 5), Mp. 48°–60° C.

(3-sulfopropyl)-(3-chlorophenyl)-ether (Ether 6);

(3-sulfopropyl)-(3-nitrophenyl)-ether (Ether 7);

(3-sulfobutyl)-(1-naphthyl)-ether (Ether 8); Mp. 86°–87° C.;

(4-sulfobutyl)-(3-methylphenyl)-ether (Ether 9); and (3-sulfobutyl)-(3-methylphenyl)-ether (Ether 10).

As indicated above, the described invention can provide for first heating the sulfoalkylating agent to an elevated temperature, such as 80°–250° C., or preferably 140°–180° C. followed by the step of adding tertiary amine. Also, the removal of an excess phenol formed may take place. These steps relate, in particular, to the production of alkane sultones, and more particularly to the production of 1,3-propane sultones and 1,4-butane sultones.

Sultones, the name being derived from "hydroxy sulfonic acid lactone", have long been known, Representatives in the aromatic, hydroaromatic and aliphatic series have been described in the literature (see the survey by J. Willems, Industrie Chimique Belge, Part XIX, page 905, 1954). The aliphatic sultones (alkane sultones) in particular have acquired widespread technical importance on account of the capacity thereof for alkylating reactions. These reactions result in the introduction of sulfoalkyl groups which considerably increase the hydrophilic character of the reactants and may even render them water-soluble. For this reason, sulfoalkyl compounds are used in the production of detergents, as well as in electroplating and in the production of sulfoalkylated dyes. Sulfoalkylated heterocyclic dyes of the polymethine and cyanine series are technologically important dyes which are used as spectral sensitizers in photography. The production thereof requires the sulfoalkylation of heterocyclic bases containing nitrogen, some of which are highly sensitive to mineral acids and hydrolysis. The use of sultones as sulfoalkylating agents is essential for the ready availability of these sulfoalkyl-substituted polymethine dyes.

Particularly important among the aliphatic sultones are the 5-membered propane sultones, in particularly 1,3-propane sultone, and the 6-membered butane sultones, in particular 1,4-butane sultone. Very varied methods have been described for the production thereof. For example in the case of propane and butane sultone, 1-chloropropane and 1-chlorobutane may be sulfochlorinated using sulfur dioxide and chlorine under exposure to light to yield chloropropane and chlorobutane sulfonic acids via the corresponding chloropropane and chlorobutane sulfochlorides, and these sulfonic acids liberate HCl under the action of heat to yield sultones (see H. H. Helberger et al, Liebigs Ann. Chem. 562, (1949), 23). Another method is based on the addition of bisulfites to unsaturated alcohols, such as allyl alcohol, and thermal elimination of water from the resulting hydroxyalkane sulfonic acids to form sultones (see J. H. Helberger, Liebigs Ann. Chem., 588, (1954), 71; and J. Willems, Bull. Soc. Chim. Belg., 64, (1955), 747).

The addition of bisulfites to unsaturated aldehydes, followed by hydrogenation to hydroxyalkane sulfonic acids used as starting compounds for the production of sultones has also been described (see C. Smith et al, J. Amer. Chem. Soc., 75, (1953), 748). Another method involves the synthesis of 1,4-butane sultone starting from 4,4'-dichlorodibutyl ether, which is readily available from the decomposition of tetrahydrofuran. The 4,4'-dichlorodibutyl ether reacts with sulfite to form the corresponding dibutyl ether-4,4'-disulfonic acid which may be converted by heat into 1,4-butane sultone (see J. H. Helberger and H. Lantermann, Liebigs Ann. Chem., 586, (1954), 158, or Org. Synthesis Coll., Vol. IV (1963), 529).

The synthesis of 2,4-butane sultone from the corresponding methoxybutanesulfonic acid by thermal ring closure is also known (see J. H. Helberger et al, Liebigs Ann. Chem., 586, (1954), 155), but this reaction is accompanined by the release of methanol which in many cases interferes with subsequent reactions. All these known methods have the major disadvantage that they are accompanied by the release of water, alcohols or mineral acids so that when the sultones produced by those methods are to be used as sulfoalkylating agents for compounds which are sensitive to mineral acids or to solvolysis, they must first be distilled. Distillation of the sultones is, however, to be avoided as far as possible for reasons of cost, as well as on account of the health risk involved since most sultones have a carcinogenic potential which is in some cases considerable.

There was therefore an interest in minimizing the environmental and safety risk entailed by the use of those alkane sultones as well as there was an interest in finding a process for the production of those alkane sultones which would not have the disadvantages mentioned above. A particular feature of the invention relates therefore also to the process to the production of alkane sultones corresponding to the following general formula IV

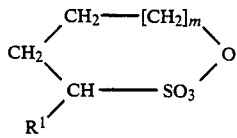

IV wherein
R¹ represents hydrogen or methyl; and
m represents 0 or 1;
characterised by the thermal decomposition at elevated temperatures of sulfoalkylaryl-ethers corresponding to formula I.

The thermal decomposition reaction takes place at a temperature of from 80° to 250° C., preferably from 140° to 170° C. The phenol resulting from the decomposition is suitably distilled off under a vacuum which should be adjusted so that the phenol may be rapidly distilled off while the sultone which is formed is left in the reaction vessel where it may undergo further reaction. However, the sultone formed may also be distilled off under reduced pressure as in the known methods. There is no difficulty in separating the phenol and sultone by distillation since they have considerably different boiling points. A distillation column is generally not required.

A particular advantage of the process according to the present invention lies in the fact that no alkanol is released in the thermal decomposition reaction and that in contrast to the byproducts formed in the known processes for the production of alkane sultones, the phenol formed as byproduct in this reaction has only a slight solvolytic reactivity so that its presence in most cases does not interfere with subsequent reactions. The sultone may therefore be subjected to further processes in the same vessel in which it was produced. It is a feature of this particular invention that the alkane sultone is reactable with sulfoalkylatable compounds in the reaction vessel. This means that sulfoalkylations may be carried out in closed apparatus without transfer of the alkane sultones from one vessel to another, and contamination of the atmosphere may therefore be safely prevented.

This also applies when the alkane sultone formed is subjected to purification by distillation in a closed apparatus and is then subjected to further reactions in the distillation receiver. Thus the alkane sultone is transferable from the reaction vessel to a distillation receiver by distillation under reduced pressure in which additional vessel the distilled and purified alkane sultone is reactable with sulfoalkylatable compounds.

Since thermal decomposition proceeds so smoothly, the sulfoalkyl-aryl ethers are suitable precursor compounds for the alkane sultones used as sulfoalkylating agents.

Since the sulfoalkyl-aryl ethers may also be obtained by the reaction of sodium or potassium phenolates with alkane sultones they constitute a physiologically and ecologically harmless "transport form" for alkane sultones.

The process according to the present invention is illustrated by the following examples.

EXAMPLE 1

1,3-propane sultone (a) 254 g of K-3-sulfopropyl-phenyl ether (potassium-3-phenoxy-propane sulfonate) (or 238 g of Na-3-sulfopropyl-phenyl ether) were suspended in 0.6 l of acetone, 110 g of concentrated hydrochloric acid were added and the mixture was stirred for 1 hour at room temperature. The precipitated KCl (NaCl) was filtered off and the acetone was distilled from the filtrate under normal pressure. The remaining 3-phenoxy-propane sulfonic acid was then decomposed by heating to from 140° to 160° C. at 7 to 18 mb, the phenol distilling off at a head temperature of from 90° to 120° C. A mixture of 0.63 mol of propane sultone and 0.32 mol of 3-phenoxypropane sulfonic acid, as well as residues of undistilled phenol were left behind. The mixture could be used without further purification as sulfopropylating agent instead of 1,3-propane sultone. When such reactions are carried out by a known method without distillation of the sultone, they do not lead to the desired product or only in low yields (see Examples 4 and 5).

(b) 254 g of K-3-sulfopropyl-phenyl ether (1 mol) were converted into the free acid as indicated under (a) and subjected to thermal decomposition at from 140° to 180° C. and under a pressure of 7 to 18 mb. 0.82 mol of phenol distilled off at from 90° to 120° C. and 0.86 mol of pure 1,3-propane sultone distilled off at a steam temperature of from 160° to 167° C.

EXAMPLE 2

3-methyl-1,3-propane sultone (a) 282 g (1 mol) of K-3-(3-methylphenoxy)-1-methylpropane sulfonate were suspended in 0.8 l of acetone and stirred with 100 ml of concentrated hydrochloric acid at room temperature for 30 minutes. The precipitated potassium chloride (98% of theoretical yield) was suction filtered and the filtrate was evaporated under normal pressure. The residue was heated to from 160° to 170° C. under a pressure of 7 to 18 mb. m-cresol first distilled off at 114°-127° C./7 mb (yield: 84 g), followed by 3-methyl-1,3-propane sultone at 154°-161° C./7 mb.
Yield: 125.6 g=92% of theoretical yield.

(b) By the reaction of 1 mol of the potassium sulfonate with hydrochloric acid as described under (a) and thermal decomposition of the ether acid at from 160° to 170° C. with removal of the m-cresol formed (0.75 mol) by distillation. A mixture of 3-m-cresyloxy-1-methylpropane sulfonic acid (24%) and 76% of 3-methyl-1,3-propane sultone was left as residue, which could be directly used as sulfoalkylating agent.

EXAMPLE 3

1,4-butane sultone

By a method analogous to Example 2(a) from 282 g of potassium-4-(3-methylphenoxy)-butane sulfonate.
Yield: 127 g (93% of theoretical yield)
b.p.: 160° C./18 mb.

EXAMPLE 4 (according to the present invention)

Anhydro-2-methyl-3-(3-sulfopropyl)-5-phenyl-benzoxazolium hydroxide; m.p. 289°-290° C.

0.85 mol of phenoxypropane sulfonic acid were cyclised to propane sultone by heating as described in Example 1(a) and removal of the phenol by distillation. After the addition of 0.85 mol of 2-methyl-5-phenyl-benzoxazole, the reaction mixture was heated to 175° C. for 1.5 hours with stirring. It was then worked up with ethanol.
Yield: 230.7 g=82% of theoretical yield.

EXAMPLE 5

(comparison; not according to the present invention)
Anhydro-2-methyl-3-(3-sulfopropyl)-5-phenyl-benzoxazolium hydroxide; m.p. 286°-289° C.

0.85 mol of 3-methoxypropane sulfonic acid, produced by the method of Helberger et al (Liebigs Ann. Chem., 586, (1954), 149, 154), was cyclised at from 160° to 165° C. in a manner analogous to Example 4 with removal of the methanol by distillation and then reacted with 2-methyl-5-benzoxazole at 175° C.
Yield: 140.6 g=50% of theoretical yield.

The process of the present invention includes the production of a sulfoalkylating agent consisting substantially of a propane or butane sultone (IV) or consisting of a mixture of one of said sultones with a corresponding phenoxy alkane sulfonic acid (I) and residues of the undistilled phenol remaining from the distillation step. The process of the present invention includes also the preparation of sulfoalkyl quaternary salts of tertiary amines by the reaction of tertiary amine with a sulfoalkylaryl ether according to the invention and its variations are further illustrated by the following Examples.

EXAMPLE 6

Anhydro-2-methyl-3-(3-sulfopropyl)-benzothiazolium hydroxide, mp. 277°-279° C.

2-Methyl-benzothiazole was boiled with its own weight of Ether 1 in 10 times the quantity of anisole for 7 hours. After cooling, the product was suction-filtered and washed with acetone.
Yield: 60.3%.

EXAMPLE 7

Anhydro-2-methyl-3-(3-sulfopropyl)-naphtho[1,2-d]oxazolium hydroxide, Mp. 270°-273° C.

(a) 2-Methyl-naphtho[1,2-d]oxazole and Ether 1 in a molar ratio of 1:1 were heated to 180° C. for 3 hours. The reaction mixture was taken up in ethanol after cooling and crystallized overnight.
Yield: 60%.

A further quantity of quaternary salt may be obtained from the mother liquor.

(b) The same as (a) but using Ether 2 instead of Ether 1.

(c) The same as (a) but using Ether 3 instead of Ether 1.
Yield: 50%.

(d) The same as (a) but using Ether 4 instead of Ether 1.

EXAMPLE 8

Anhydro-2,5-6-trimethyl-3-(3-sulfopropyl)-benzothiazolium-hydroxide, Mp. 291° C.

Analogous to Example 7, from 2,5,6-trimethyl-benzothiazole and Ether 1 in 5 hours at 180° C.
Yield: 61%.

EXAMPLE 9

Anhydro-2-methyl-3-(3-sulfopropyl)-naphtho[1,2,-d]thiazolium hydroxide, Mp. 273°-275° C.

Analogous to Example 4, from 2-methylnaphtho[1,2-d]thiazole and Ether 2 in a molar ratio of 1:1.5 in 5 hours at 180° C.
Yield: 74%.

EXAMPLE 10

Anhydro-1,2-dimethyl-5,6-dichloro-3-(3-sulfopropyl)-benzimidazolium hydroxide, Mp. 300° C.

Analogous to Example 7, from 1,2-dimethyl-5,6-dichloro-benzimidazole and Ether 2 in 3 hours at 180° C.,
Yield: 70%.

EXAMPLE 11

Anhydro-3-(3-sulfopropyl)-4,5-benzo-3'-ethyl-5'-phenyloxacarbocyanine hydroxide (a) 2-methylnaphtho[1,2-d]oxazole (1/200 mol) and Ether 1 in a molar ratio of 1:2 were heated to 180° C. for 3 hours. The reaction mixture was taken up with 25 ml of ethanol and after the addition of 1/200 mol of 2-(2-phenyl-iminoethylidene)-5-phenyl-3-ethyl-benzoxazole, 0.5 ml of acetic anhydride and 2 ml of triethylamine, the mixture was stirred for 5 minutes at 50° C. After it had been left to stand overnight, the dye was isolated by suction filtration and washed with ethanol.
Yield: 88% absorption maximum in methanol 506 nm, Mp. 267°-268° C.

(b) As under (a), using Ether 2: Yield: 68%.
(c) As under (a), using Ether 3: Yield: 64%.
(d) As under (a), using Ether 4: Yield: 60%.
(e) As under (a), using Ether 6: Yield: 52%.

EXAMPLE 12

2-[2-(3-ethyl-2-thioxo-4-oxo-5-thiazolidinylidene)-ethylidene]-3-(3-sulfopropyl)-5-methyl-6-methoxybenzoselenazole, triethylamine salt.

(a) 1/200 mol of 2,5-dimethyl-6-methoxybenzoselenazole and 0.0075 mol of Ether 2 were heated to 180° C. for 3 hours. The melt was taken up with 10 ml of ethanol, and 1.1 g of 5-ethoxy methylene-3-ethyl rhodanine and 2 ml of triethylamine were then added. The reaction was completed after 5 minutes at 50° C.
Yield: 68%. Absorption maximum: 544 nm.

(b) As under (a), by 3 hours quaternization at 160° C. in the presence of 0.5 ml of acetic anhydride;
Yield: 49%.

EXAMPLE 13

Anhydro-3-ethyl-3'-(3-sulfobutyl)-5,5'-diphenyl-oxacarbocyanine hydroxide (a) 0.005 mol of 5-phenyl-benzoxazole and 0.01 mol of Ether 10 were heated to 180° C. for 3 hours. The resulting mass was taken up with 10 ml of ethanol and to it were added 0.005 mol of 2-(2-phenyliminoethylidene)-3-ethyl-5-phenyl-benzoxazole, 0.5 ml of acetic anhydride and 2 ml of triethylamine, and the mixture was stirred for 5 minutes at 50° C.
Yield: 70%. Absorption maximum: 496 nm.

(b) As under (a), by quaternization in the presence of 0.5 ml of acetic anhydride for 3 hours at 160° C.;
Yield: 69%.

EXAMPLE 14

Anhydro-3,3'-bis-(3-sulfopropyl)-4,5-benzothiacyanine hydroxide, triethylamine salt 0.005 mol of 2-mercaptobenzothiazole and 0.0075 mol of Ether 2 were heated to 160° C. for 5 hours. The reaction mixture was then dissolved in 20 ml of ethanol so that the S,N-bis-(3-sulfopropyl) derivative which had formed in the reaction mixture could be reacted with 1.6 g of anhydro-2-methyl-3-(3-sulfopropyl)-naphtho[1,2-d]thazolium hydroxide in the presence of 2 ml of triethylamine at 60° C. for 10 minutes.
Yield: 55%. Absorption maximum in methanol: 442 nm.

EXAMPLE 15

3-Ethyl-5-[3-(3-sulfopropyl)-5-methylthio-1,3,4-thiadiazolin-2-ylidene]-rhodanine, pyridine salt 0.1 mol of 2,5-bis-methylthio-1,3,4-thiadiazole and 0.2 mol of Ether 2 were heated to 140° C. for 3 hours. The reaction product was taken up with 50 ml of pyridine and after the addition of 0.1 mol of 3-ethyl rhodanine up to a temperature of 80° C., the reaction mixture was stirred for 5 hours at room temperature.
Yield: 52%. Absorption maximum in water: 422 nm.

EXAMPLE 16

Anhydro-1-ethyl-1'-(3-sulfopropyl)-2,2'-cyanine hydroxide 0.005 mol of quinaldine and 0.01 mol of Ether 2 were heated to 180° C. for 3 hours. After cooling to 60° C., 15 ml of ethanol, 0.005 mol of 1-ethyl-2-ethylthio-quinolinium-ethyl sulfate and 2 ml of triethylamine were added. The reaction was completed after 20 minutes at 60° C. The dye was precipitated with aqueous acetone.
Yield: 10%. Absorption maximum in methanol: 525 nm.

EXAMPLE 17

Anhydro-2-methyl-5-phenyl-3-(3-sulfopropyl)-benzoxazolium hydroxide (a) 0.005 mol of 2-methyl-5-phenyl-benzoxazole, 0.0075 mol of Ether 2 and 0.5 ml of acetic acid anhydride were heated to 180° C. for 3 hours. After cooling, 10 ml of ethyl acetate and 4 ml of 1-propanol were added to crystallize the reaction product.
Yield: 85%; Mp. 280°–283° C.

(b) 12.9 g of Ether 1 were heated to 140° C. for two hours. After addition of 10.5 g of 2-methyl-5-phenyl-benzoxazole the mixture was heated to 175° C. for 3 hours and then, after cooling, was worked up with ethanol.
Yield: 13.9 g (84%); Mp. 288°–290° C.

EXAMPLE 18

Anhydro-2-methyl-5-chloro-3-(4-sulfobutyl)-benzothiazolium hydroxide 3.6 g of 2-methyl-5-chlorobenzothiazole and 7.2 g of Ether 9 were heated to 175° C. for 4 hours. The reaction product was worked up with acetone.
Yield: 74%. Decomposition 295° C.

EXAMPLE 19

Anhydro-2,5,6-trimethyl-3-(4-sulfobutyl)-benzothiazolium hydroxide

Analogous to Example 18, from 2,5,6-trimethyl-benzothiazole and Ether 9.
Yield: 74%. Decomposition: 293°–295° C.

What is claimed is:

1. The process for the preparation of sulfoalkyl quaternary salt of a tertiary amine by reacting the tertiary amine with a sulfoalkylating agent at an elevated temperature, wherein
(a) The tertiary amine corresponds to the following general formula II

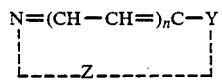

wherein
Y represents hydrogen, halogen, a saturated or unsaturated aliphatic group containing up to 6 carbon atoms; alkoxy, alkylthio or mercapto;
Z represents the members required for completing a heterocyclic group comprising at least one 5- or 6-membered heterocyclic ring; and
n=0 or 1;
(b) the sulfoalkylating agent is a sulfoalkylaryl ether of the following general formula

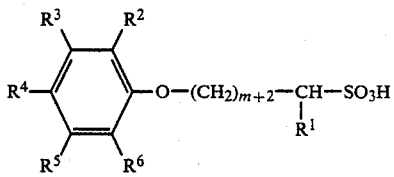 (I)

wherein
R$^1$ represents hydrogen or methyl;
R$^2$, R$^3$, R$^4$, R$^5$, R$^6$ represent hydrogen, alkyl having 1 or 2 carbon atoms, halogen, OCH$_3$, cyano or nitro (but not more than 2 nitro groups are present in the phenyl ring); or R$^3$ together with R$^2$ or R$^4$ represent ring members required for completing a condensed 5- or 6-membered ring; and
m=0 or 1; and
(c) the sulfoalkylating reaction is carried out at a temperature in the range of from 100° to 250° C.

2. The process as claimed in claim 1 in which the reaction is carried out at a temperature of from 140° to 180° C.

3. The process as claimed in claim 2 in which the reaction is carried out in the presence of a solvent.

4. The process as claimed in claim 2 in which the reaction is carried out in the presence of acetic anhydride.

5. The process as claimed in claim 2 in which the sulfoalkylating agent is heated to the elevated temperature before the tertiary amine is added.

6. The process for the production of alkane sultones corresponding to the following general formula IV:

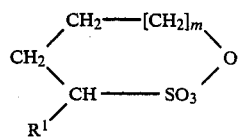 IV wherein
R$^1$ represents hydrogen or methyl; and
m represents 0 or 1; characterised by thermal decomposition at elevated temperatures of sulfoalkyl-aryl ethers corresponding to the following general formula I:

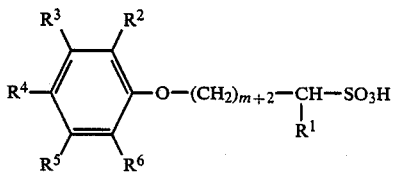 I wherein
R$^1$ represents hydrogen or methyl;
R$^2$, R$^3$, R$^4$, R$^5$ and R$^6$ represent hydrogen, alkyl having 1 or 2 carbon atoms, halogen, OCH$_3$, or nitro (but not more than 2 nitro groups are present in the phenyl ring) or R$^3$ together with R$^2$ or together with R$^4$ represent the ring members required for completing a condensed 5- or 6-membered ring; and
m=0 or 1 wherein said substituents R$^2$, R$^3$, R$^4$, R$^5$ and R$^6$ do not impair thermal decomposition.

7. The process as claimed in claim 6, wherein the thermal decomposition is carried out at from 140° to 170° C.

8. The process as claimed in claim 6, wherein the phenol formed in the course of thermal decomposition is completely or partly removed from the reaction vessel by distillation at reduced pressure.

9. The process as claimed in claim 8, wherein the alkane sultone is reacted with tertiary amine compounds in the reaction vessel.

10. The process as claimed in claim 8 wherein after removal of the phenol the remaining alkane sultone is transferred to a distillation receiver by distillation under reduced pressure and reacted therein with tertiary amine compounds.

11. The process for the preparation of sulfoalkyl quaternary salt of a tertiary amine by reacting the tertiary amine with a sulfoalkylating agent at an elevated temperature, wherein
(a) The tertiary amine corresponds to the following general formula II

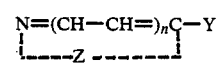

wherein
Y represents hydrogen, halogen, a saturated or unsaturated aliphatic group containing up to 6 carbon atoms; alkoxy, alkylthio or mercapto;
Z represents the members required for completing a heterocyclic group comprising at least one 5- or 6-membered heterocyclic ring; and
n=0 or 1;
(b) the sulfoalkylating agent is a sulfoalkylaryl ether of the following general formula I

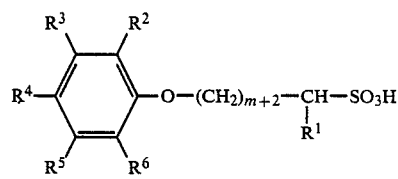 (I)

wherein
R$^1$ represents hydrogen or methyl;
R$^2$, R$^3$, R$^4$, R$^5$, R$^6$ represent hydrogen, alkyl having 1 or 2 carbon atoms, chlorine or nitro (but not more than 2 nitro groups are present in the phenyl ring); or R$^3$ together with R$^2$ or R$^4$ represent ring members required for completing a condensed 6-membered ring;
m=0 or 1; and
(c) the sulfoalkylating reaction is carried out at a temperature in the range of from 100° to 250° C.

12. A sulfoalkylating agent for tertiary amines free of alkanol comprising the product of thermal decomposition of elevated temperatures of sulfoalkylaryl ethers corresponding to the following general formula:

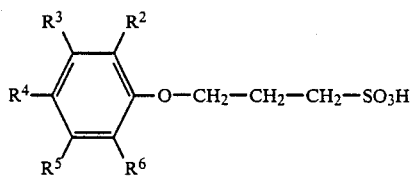

in which formula

R², R³, R⁴, R⁵ and R⁶ represent hydrogen, alkyl having 1 or 2 carbon atoms, halogen, OCH₃ or nitro (but not more than 2 nitro groups are present in the phenyl ring; or R³ together with R² or together with R⁴ represents the ring members for completing a condensed 5- or 6-membered ring; wherein the phenol formed in the course of thermal decomposition is completely or partly removed from the reaction vessel by distillation at reduced pressure.

13. The sulfoalkylating agent for tertiary amines as claimed in claim 12 consisting substantially of 1,3-propane sultone or of a mixture of 1,3-propane sultone and a phenoxypropane sulfonic acid.

* * * * *